United States Patent [19]
Gustilo et al.

[11] Patent Number: 5,733,292
[45] Date of Patent: Mar. 31, 1998

[54] ARTHROPLASTY TRIAL PROSTHESIS ALIGNMENT DEVICES AND ASSOCIATED METHODS

[75] Inventors: Ramon B. Gustilo, Eden Prairie; Richard S. Hammett, Minneapolis; William D. Lew, Mendota Heights; Joan E. Bechtold, Minneapolis, all of Minn.

[73] Assignee: Midwest Orthopaedic Research Foundation, Minneapolis, Minn.

[21] Appl. No.: 529,243

[22] Filed: Sep. 15, 1995

[51] Int. Cl.⁶ .................... A61B 17/56
[52] U.S. Cl. .................... 606/88; 606/86; 606/89; 606/90; 606/99
[58] Field of Search .................... 606/88, 89, 90, 606/99; 623/18, 20, 16

[56] References Cited

U.S. PATENT DOCUMENTS

| | | |
|---|---|---|
| 4,457,307 | 7/1984 | Stillwell . |
| 4,474,177 | 10/1984 | Whiteside . |
| 4,501,266 | 2/1985 | McDaniel . |
| 4,566,448 | 1/1986 | Rohr, Jr. . |
| 4,567,885 | 2/1986 | Androphy . |
| 4,646,729 | 3/1987 | Kenna et al. . |
| 4,653,488 | 3/1987 | Kenna . |
| 4,703,751 | 11/1987 | Pohl . |
| 4,718,413 | 1/1988 | Johnson . |
| 4,722,330 | 2/1988 | Russell et al. . |
| 4,759,350 | 7/1988 | Dunn et al. . |
| 4,773,407 | 9/1988 | Petersen . |
| 4,825,857 | 5/1989 | Kenna . |
| 4,892,093 | 1/1990 | Zarnowski . |
| 4,892,546 | 1/1990 | Kotz et al. . |
| 4,907,578 | 3/1990 | Petersen . |
| 4,926,847 | 5/1990 | Luckman . |
| 4,935,023 | 6/1990 | Whiteside et al. . |
| 4,938,762 | 7/1990 | Wehrli . |
| 5,002,547 | 3/1991 | Poggie et al. . |
| 5,037,423 | 8/1991 | Kenna . |
| 5,098,436 | 3/1992 | Ferrante et al. . |
| 5,122,144 | 6/1992 | Bert et al. . |
| 5,129,909 | 7/1992 | Sutherland . |
| 5,197,488 | 3/1993 | Kovacevic . |
| 5,213,112 | 5/1993 | Niwa et al. . |
| 5,228,459 | 7/1993 | Caspari et al. . |
| 5,234,433 | 8/1993 | Bert et al. . |
| 5,250,050 | 10/1993 | Poggie et al. . |
| 5,312,411 | 5/1994 | Steele et al. . |
| 5,342,367 | 8/1994 | Ferrante et al. . |
| 5,364,401 | 11/1994 | Ferrante et al. . |
| 5,364,402 | 11/1994 | Mumme et al. . |
| 5,489,311 | 2/1996 | Cipolletti .................... 623/20 |

*Primary Examiner*—Michael Buiz
*Assistant Examiner*—Daphna Shai

[57] ABSTRACT

An adjustable trial prosthesis or prosthetic component provides a surgeon with the capability of efficiently and accurately examining a joint's functioning without having to remove a trial prosthesis insert and replace it with another sterilized insert. The adjustable trial has a first surface that approximates the top surface of the corresponding permanent prosthesis and a second surface that engages a bone. A distance adjustment mechanism can alter the distance between the first and second surfaces. The distance adjustment mechanism can include a screw oriented generally between the two surfaces or other distance adjustment mechanisms such as a fluid filled bladder. The adjustable trial can include force transducers to provide information on forces within the joint. To assist a surgeon with the alignment of portions of the musculo-skeletal system, a line of strong light is provided. The light source can be a laser or other suitable light source which is combined with appropriate optics. A balancing apparatus can be used to assess relative tensions on peri-articular soft tissue structures. The balance has a support that is adapted for rigid attachment directly or indirectly to a bone.

11 Claims, 14 Drawing Sheets

1

ARTHROPLASTY TRIAL PROSTHESIS ALIGNMENT DEVICES AND ASSOCIATED METHODS

FIELD OF THE INVENTION

The invention relates to devices to assist with joint arthroplasty especially, knee arthroplasty and total knee arthroplasty. More specifically, the invention relates to devices that assist with determining the proper size for permanent prostheses while also achieving proper ligament tension and joint alignment.

BACKGROUND OF THE INVENTION

Although the devices described by the invention are adaptable for most joints, the discussion focuses on but is not limited to knee joints. The knee joint provides flexing of the leg where a lower bone called the tibia meets an upper bone called the femur. The femur at the knee has two projections known as femoral condyles that engage fibro-cartilage at the upper end of the tibia. The joint is held together by ligaments, capsule, and muscle and tendons. Four ligaments are especially prominent in the knee structure with one ligament on either side of the knee and two in the center of the knee with one oriented toward the front and one toward the back. The patella or knee cap is a piece of bone supported in front of the joint to act as a shield.

During total knee arthroplasty, i.e., replacement surgery, it is important for obtaining normal function over a long period of time to have proper tension in the ligaments and other soft tissues surrounding the knee, and proper alignment of the leg. The weight of the person is transferred from the head of the femur at the hip to the ankle. Proper alignment of the knee will allow the proper transfer of forces over the two sides of the knee. Each side of the knee is supported by ligaments and other tissues. These soft tissues help hold the surfaces of the tibia and femur in proper relative position. A normal knee will have equal tension in the soft tissues and weight distributed equally on the two sides of the knee. Of course, the alignment and balance of tensions are closely related. The ultimate objective is to obtain equal tensions when the knee is aligned.

During total knee arthroplasty, the two surfaces joining at the knee are replaced. The first step in this process is the removal of the natural material. The distal end of the femur is cut in order to provide clearance for a femoral component of the knee prosthesis that provides one new surface. Similarly, the tibia is cut to provide a relatively flat surface for a tibial component of the knee prosthesis that has a base with an insert that provides the mated surface for the femoral component.

In order to select the proper size tibial component insert, a number of trial inserts are selected to put in place on a trial tibial component base. The insert must have the correct size in terms of the extent of the surface to match the corresponding femoral component, and of the thickness to provide tension in the collateral ligaments and other soft tissues.

The size and thickness of the tibial component insert can be estimated from imaging prior to starting the operation, but the final thickness must be determined during surgery. For example, with the Genesis™ knee prosthesis system, there are 10 thicknesses between 8 mm to 35 mm for each of 6 surface sizes from small to magnum plus. Then, for this system there would be sixty possible trial tibial inserts that may need to be sterilized and tested during surgery. Other knee prosthesis systems have a comparable number of trial inserts.

Contact between the tibial component insert and the femoral component should create the proper tension in the ligaments and other soft tissues on the sides of the knee. The thickness of the insert is selected to provide this tension. Furthermore, with the prosthesis in place the leg should be properly aligned, and the ligaments and the other soft tissues on both sides of the knee should have roughly equal tension.

Alignment of the leg is traditionally checked using a long straight metal rod. One end of the metal rod is aligned with the center of the femoral head and the other end is aligned with the center of the ankle. The center of the femoral head is determined either from an x-ray before surgery or, less preferably, by the point located the width of three fingers medial to the anterior superior iliac spine. When aligned, the rod should bisect the center of the knee components.

When the leg is straight, the soft tissues at the knee should have equal tension. The relative tensions of the soft tissues may be first adjusted before the tibial component trials are put in place. These initial adjustments can be made based on expected problems from an x-ray view of the knee before surgery. The ligaments are adjusted by soft tissue releases to loosen the soft tissues on the tighter side of the knee. Then, after placement of a tibial trial component insert of approximately the correct size and after the alignment is checked, the ligament and soft tissue tension is checked with the leg extended and flexed. If the tissues on the sides of the knee are not of equal tension, soft tissue releases are performed on the side of the knee with higher tension. If soft tissue releases are performed after the selection of a particular trial component, the trial thickness will have to be adjusted again, and the alignment of the knee rechecked. This process is repeated until the alignment and soft tissue tensions are simultaneously correct.

The process of aligning the knee and achieving proper soft tissue tension has historically relied heavily on the skill and experience of the surgeon. Even for the most skilled surgeons, this can be a slow process in terms of selecting the proper tibial trial component and obtaining the proper alignment and tension in the ligaments and capsular soft tissues.

Known devices assist with balancing the soft tissues by attachment to the knee from the outside and holding the tibia and femur apart. For example, spreaders can be inserted on either side of a knee to apply tension to the tissues on both sides of the knee. The alignment can then be corrected by appropriate soft tissue releases. One limitation with this apparatus is that the tensioning is not performed with the prosthesis in place. Since the alignment and tensions may not be the same after the trial prosthesis components are installed, it may be necessary to repeat the alignment and tensioning operations.

Also, the knee cannot be moved between the flexed and extended positions with the spreaders in place. To change from an extended to a flexed position, the spreaders must be removed. It is important to achieve balance in both the extension and flexion positions since the flexion gap and the extension gap are different. Great care must be taken in placing the spreaders to prevent applying lateral forces with the spreaders that will distort the balancing of the tensions.

U.S. Pat. No. 4,566,448 (Rohr, Jr.) discloses a device that externally grips the generally flat surface of the cut tibia and the intercondylar notch of the femur. The adjustment of a screw separates the tibia and femur to tense the ligaments. This device has the disadvantages of the spreader discussed above. Furthermore, since the device extends from the front of the knee, the knee cannot be continuously flexed and extended because the patella cannot be relocated. The placement of the device limits assessment of patella trcking and restricts checking the soft tissue balance at only a fixed flexion or extension angle. The device does additionally provide a cutting guide for the condyles of the femur.

U.S. Pat. No. 4,501,266 (McDaniel) describes an apparatus that fits around the knee to adjust the force on either side to select appropriate soft tissue tension. Alignment is simultaneously examined with a metal rod as the tension is adjusted. The purpose is to establish both proper total tension and balance between the tissues on the two sides of the knee. This device has possible advantages over the spreaders because of the measurement of the force and because of the design which helps ensure that the forces on the two sides of the knee are properly balanced. But this device has some of the limitations of the spreaders because a trial prothesis is not in place and the knee cannot be repositioned while the device is in place. The accuracy achieved by adjusting the alignment and tension before the knee is prepared for the prostheses is not as high as the accuracy of the invention described below.

This device also has a metal rod that can be attached to check the alignment with the top of the femur. The problems with the use of metal rods are the awkwardness of using, sterilizing and storing such devices, the additional time required to use them which extends the time of the patient under anesthesia, and the difficulty in obtaining an accurate reading because they tend to bend.

Since the above devices do not tense the supporting tissue with a structure comparable with the eventual prosthesis, the surgeon must rely on experience to make final adjustments with the tibial trial component in place. Still, this final tensioning of the tissues is performed by hand. This is complicated by the fact that the supporting tissue on each side of the knee has multiple fibers which may have different tensions. Caution is needed to ensure that comparable fibers are being compared on the two sides of the knee.

U.S. Pat. No. 5,197,488 (Kovacevic) depicts a force transducer that fits between a femoral component and a tibial trial base. Unlike the tensioners described above, this transducer approximates the structure of the final prosthesis so that the instrument should measure the approximate forces with the final prosthesis in place. The problem with this approach is that the transducer-like standard tibial trials must be fit to the individual. It is expensive to instrument the large number of tibial trial inserts in the respective sizes. Also, it will take a large amount of time to make force measurements for all of the different sizes of transducers.

SUMMARY OF THE INVENTION

The instruments of the present invention improve the efficiency and accuracy of the fitting of joint prostheses. Specifically, an adjustable trial component provides the surgeon with the capability of examining a joint's function efficiently and accurately without having to remove the trial component insert and replace it with another sterilized insert. This adjustable trial can be used very effectively with other instruments of the invention which assist with alignment.

The adjustable trial has a first surface that approximates the top surface of the permanent prosthesis on a first bone of the joint. The first surface has relatively low friction contact with the outer surface of the prosthesis or prosthetic component on the opposing bone. The adjustable trial has a second surface that engages the first bone so that the adjustable trial is stably situated between the two bones of the joint. The second surface approximates a corresponding surface on the permanent prosthesis. A distance adjustment mechanism can alter the distance between the first and second surfaces.

The distance adjustment mechanism can include a screw that is operably engaged with and rotationally uncoupled from one of the surfaces. Threads mated with the screw are attached to the other surface. Rotation of the screw relative to the threads therefore changes the distance between the two surfaces. The adjustable trial may have stops that preferentially resist rotation of the screw at particular angular orientations of the screw. These can assist the surgeon in knowing how far the adjustment mechanism has been advanced. The first surface can be tillable relative to the second surface, so that the surgeon can use the tilting as an indication of imbalance in the forces within the joint.

Other distance adjustment mechanisms can be used such as a fluid filled bladder and a screw placed between the surfaces that is operably attached to lever arms attached to the surfaces. Rotation of the screw will change the angle between the surfaces and the lever arms, thereby changing the distances between the two surfaces. The second surfaces can have one or more posts projecting from the surface that serve to stabilize the trial component in position and/or to act as a sleeve for a screw or other component for the distance adjustment mechanism.

The adjustable trial component can have a peripheral stabilizer to help maintain the relative orientations of the first and second surfaces. Also, the adjustable trial component can include force transducers used to measure forces within the joint. These force transducers can be strain sensors. The preferred embodiment would have strain sensors located at representative locations across the adjustable trial to help ascertain the balance of forces within the joint. The instrumented trial component will measure contact forces during flexion-extension that reflect the balance and tension in the soft tissues around the joint. The force transducers can be placed within a cavity or they can be embedded within material that is continuous with the first surface.

The adjustable trial component is used to select the proper size for a permanent joint prosthesis. First, the adjustable trial with a distance adjustment mechanism is placed within the joint after necessary cuts have been made to the bone. The distance adjustment mechanism is adjusted to obtain appropriate tension of soft tissues within the joint. From this adjustment of the distance adjustment mechanism, the appropriate size for the permanent prosthesis is determined.

To assist a surgeon with alignment of portions of the musculo-skeletal system, a light forming a long line of strong light is provided. To align the light, the surgeon aligns the line of light on two points with one on each side of the region of interest. The surgeon then examines the line of light passing through the portion of interest to determine whether it is aligned. If the portion of the musculo-skeletal system is not aligned, the surgeon performs the alignment based on the line of light. The light source can be a laser, an incandescent bulb or other suitable light source. Appropriate optics are used to collimate the light into a long line.

When the portion of the musculo-skeletal system is a knee joint, the line of light is aligned with the mechanical axis, as defined by a point over the femoral head and a point through the center of the ankle. Once the line of light is positioned, the surgeon determines what portion of the knee the line of light falls on. If necessary, the knee is adjusted such that the line of light roughly bisects the knee joint and passes appropriately near the intercondylar notch. After the surgeon adjusts the knee, the surgeon can recheck that the line of light passes through the center of the femoral head and the center of the ankle.

A balancing apparatus can be used to assess the relative tension on peri-articular soft tissue structures. The balance would have a pivot arm hinged at a support. The pivot arm should be balanced when no external forces are applied. A pointer is attached to the pivot arm at a ninety degree angle to the line along the pivot arm to indicate the angle at the hinge. The support is adapted for rigid attachment to a bone such that the attachment to the prosthesis defines an orientation where the collateral ligaments and other tissues should be balanced. The lever arms have fasteners symmetric about the hinge for attaching the soft tissues to the lever arms. The fasteners can include a hook and/or a spring.

The balance can also include a level mounted to the support to adjust the knee so that the balance is oriented to produce an accurate reading of the relative tensions. To determine the relative balance, the fasteners are attached to the soft tissue, and the relative balance of the soft tissue is determined from the relative balance of the lever arms. The rigid attachment to the bone can be though direct attachment to a bone or through attachment to a prosthesis or prosthetic component in contact with the bone.

DETAILED DESCRIPTION OF THE INVENTION

Figure 1:
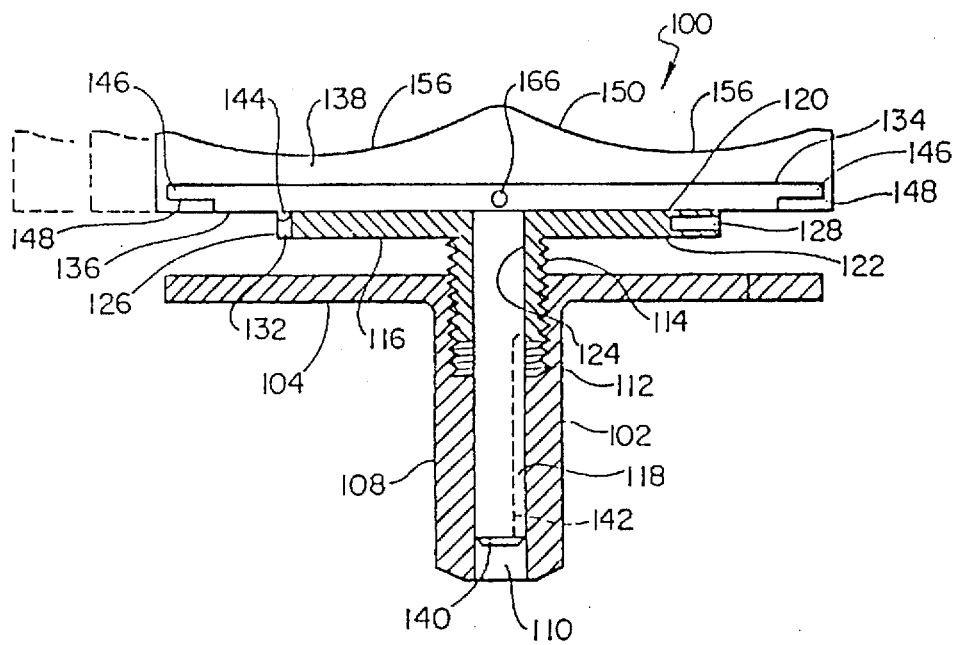
FIG. 1 is a cutaway from view of a first embodiment of an adjustable trial of the invention with a stop element displayed 90 degrees displaced relative to a central bore such that it can be displayed simultaneously with holes for accepting an advancing lever, with a notch within the post of an upper platform shown in phantom lines and with possible variation in size of an upper support also shown in phantom lines on one side of the upper platform; similar variations on the other side are not shown.

The invention involves instruments to improve the efficiency and accuracy while decreasing cost for performing orthopedic surgery, especially surgery on joints including joint replacement. Instruments according to the invention include adjustable trial prosthetic components, a light strip alignment device and a soft tissue tension balance. The adjustable trial components are used to determine the correct size for a permanent prosthesis for joint replacement. Based on the concepts disclosed here, the adjustable trial device can be adapted to the particular joint based on the structure of the joint and the structure of the appropriate permanent prosthesis. The light strip alignment device can be used generally for the alignment of portions of the musculoskeletal system. Similarly, the soft tissue tension balance can be adapted for the measurement of relative tension within desired portions of soft tissue. The descriptions below focus on knee joints.

To fit permanent prostheses, trial components are used to determine the correct sizes. In preparation for use of the trial components for joint replacement, the bones meeting at the joint are cut appropriately for the placement of the components. In the case of a knee joint, the ends of the femur and tibia are cut. In addition, appropriate holes, if any, can be made that are used to support the trial components during the sizing and alignment procedure. Depending on the design of the trial components and the permanent prosthesis, these same holes would preferably be used to support the permanent prosthesis. The adjustable trial components are used to select the appropriately sized inserts of the permanent prosthesis. For a knee joint, the proper size of the tibial component is selected.

The adjustable trial component will have, at least, three components including a lower platform, an upper support and an adjustment mechanism. For a knee joint, the lower platform of the trial corresponds to the lower platform of the permanent tibial component. Therefore, it can have various projections corresponding to projections in the lower platform of the permanent tibial component to help stabilize it by mating with the underlying bone. The upper surface of the upper support corresponds to the upper surface of the permanent insert for the tibial component. These upper surfaces are designed for low friction engagement with either the permanent or trial femoral component. The upper support should be selected to have the correct size to match the femoral component.

The function of the adjustment mechanism is to change the relative distances between the lower platform and the upper support. The distance is selected to achieve the proper tension in the ligaments and other soft tissue around the joint. With the adjustment mechanism, the surgeon can use a single trial to determine the correct thickness for the permanent tibial insert without the need to interchange trial inserts with varying thicknesses. Also, the adjustment mechanism is potentially more accurate than the replacement by fixed thicknesses of trial inserts. Therefore, the thickness of the permanent inserts can be determined without causing delay due to the need to try a larger number of trial inserts and without introducing greater risk of error by mistaking which trail is being used.

Figure 27:
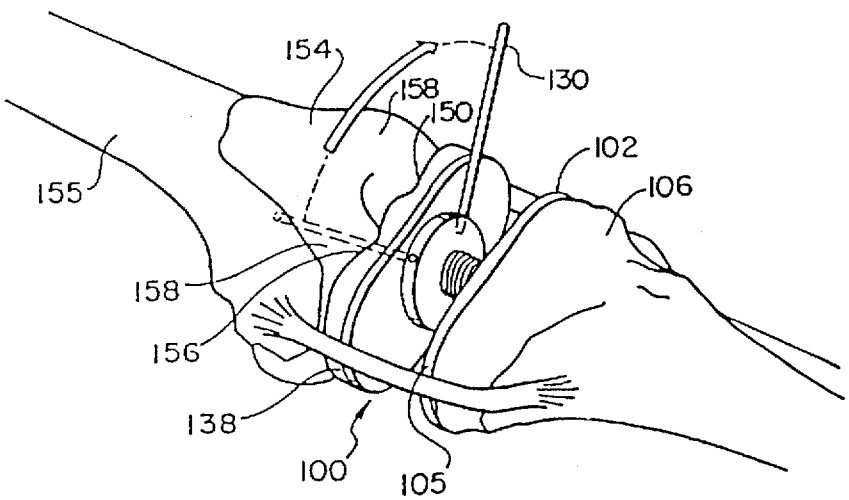
FIG. 27 is a perspective view of the first embodiment of the adjustable trial in position in a knee while contacting a femoral component with phantom lies indicating the advancement of the adjustment platform by one stop.

A first embodiment of the adjustable tibial trial 100 is shown in FIGS. 1–6. The lower platform 102 has a generally flat lower surface 104 for contacting the generally flat surface 105 of the cut tibia 106, as shown in FIG. 27. The lower platform has a post 108. The post 108 is sized for corresponding fit into a hole (not shown) drilled into the tibia 106. The post 108 will preferably have a length approximately of 66 mm for a standard trial for a normal adult, although this may vary according to patient size and prosthesis design. Post 108 may correspond to a comparable post on the permanent prosthesis (not shown) that may have a somewhat different length, shape or diameter. If the permanent prosthesis does not have a post or it has different configurations of post or posts, the lower platform can be substituted accordingly based on embodiments shown below. The lower platform 102 is preferably made of stainless steel, but other rigid materials can be used as long as they are suitable for sterilization and intraoperative implantation in the human body.

The lower platform 102 has a bore 110 extending through post 108. A portion of the bore 110 has appropriate threads 112 cut into the bore 110 sidewall at a somewhat larger diameter than the portion of the bore 110 without threads. A suitable pitch for the threads 112 is 4 mm per turn, although other pitches can be used if desired. Similar adjustments can be obtained using a double thread with a pitch of 2 mm per turn. The threads 112 are mated with screw 114 which extends from adjustment platform 116. The pitch relates to the distance change within the trial for a given rotation of the screw 114. Therefore, the pitch of the threads 112 is correlated with the accuracy obtainable in the trial spacing on the assumption that the accuracy is limited by the ability to control the rotation of the screw. The portion of bore 110 without threads 112 has an antirotation means, which in this embodiment is formed as key 118.

Figure 2:
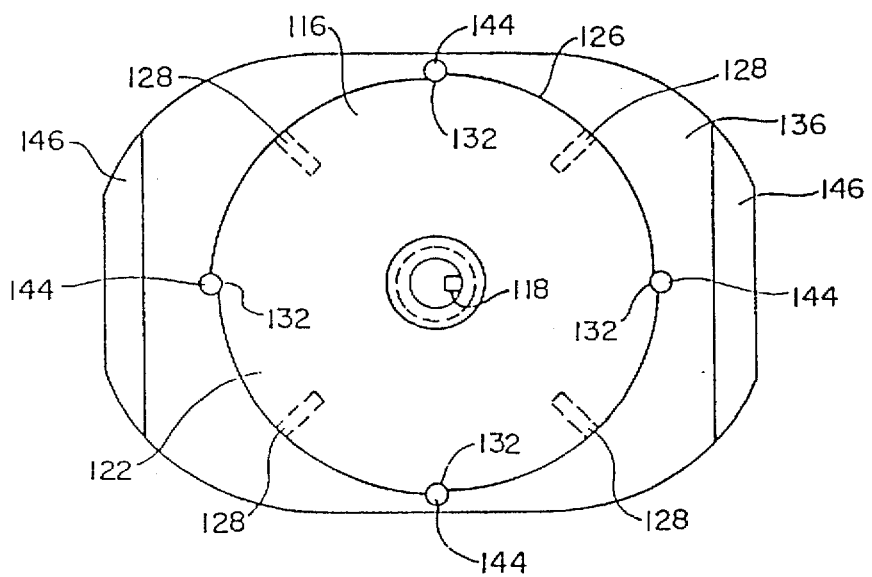
FIG. 2 is a bottom view of an upper platform engaged with an adjustment platform within the first embodiment of the adjustable trial with hidden holes for accepting an advancing lever shown in phantom lines.

The adjustment platform 116 has an upper surface 120 and a lower surface 122, as shown in FIG. 1. The distance from the upper surface 120 to the lower surface 122 should be small so that the adjustable trial will have a small minimum thickness. Screw 114 extends from the lower surface 122 of the adjustment platform 116. The adjustment platform 116 has a central bore 124 extending from the upper surface 120 completely through screw 114. Adjustment platform 116 will have an edge 126 connecting upper surface 120 and lower surface 122. As shown in FIG. 2, this embodiment has four apertures or holes 128 in edge 126 for insertion of advancing lever 130, shown in FIG. 5, or other suitable device. Holes 128 are spaced every 90 degrees around edge 126. Similarly, four stops 132 are located every 90 degrees around the edge 126. Each stop 132 is placed between a pair of holes 128. Of course, different arrangements of holes and stops can be effectively used.

Adjustment platform 116 is preferably made from high density polyethylene, nylon or metal, although other materials or combination of materials would be suitable. When screw 114 is engaged with threads 112 in lower platform 102, central bore 124 in adjustment platform 116 lines up with bore 110 in lower platform 102. Upper surface 120 of adjustment platform 116 engages upper platform 134 at its lower surface 136 with relatively low friction contact such that adjustment platform 116 can rotate relative to upper platform 134 when the surgeon moves advancing lever 130.

Figure 5:
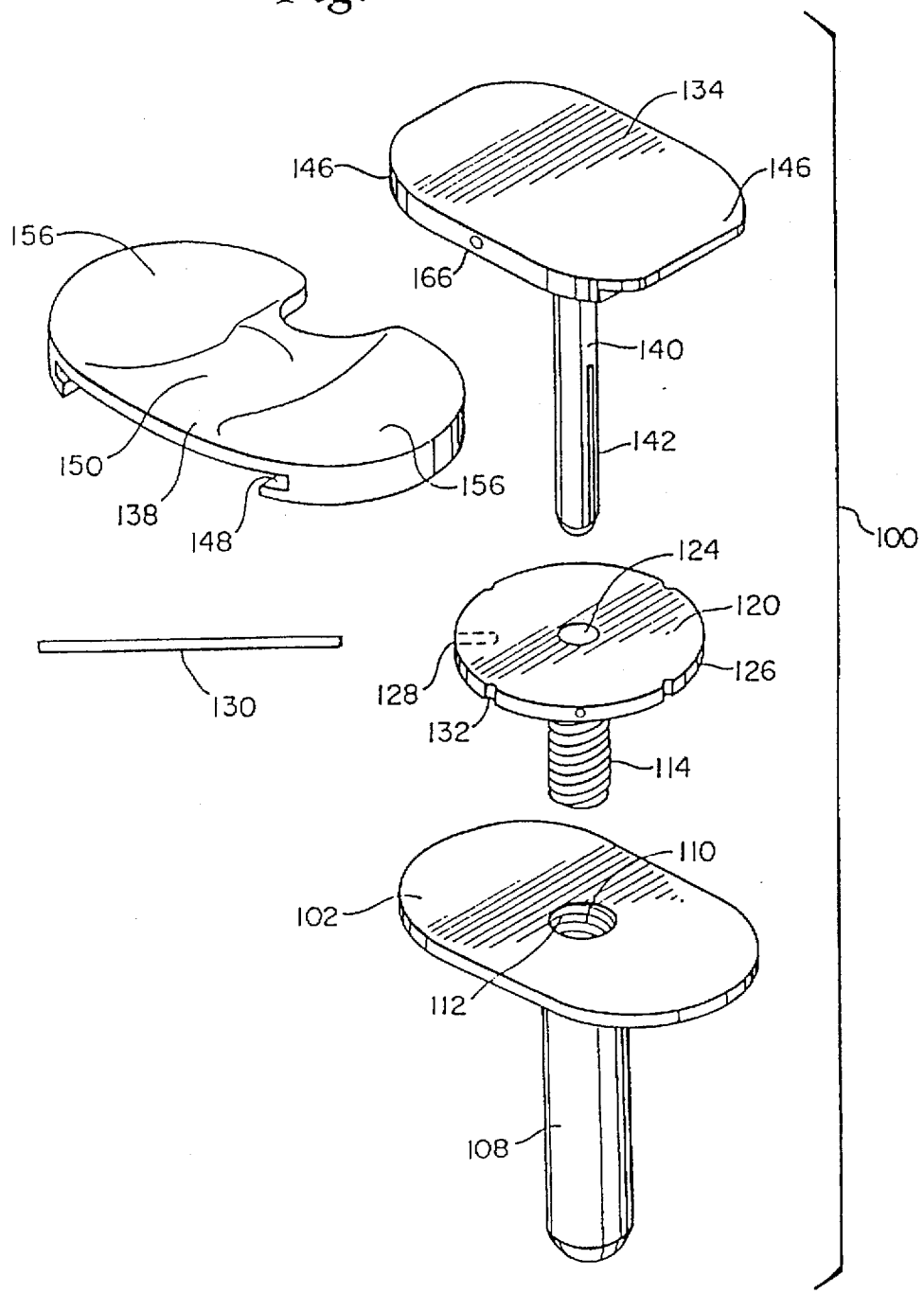
FIG. 5 is an exploded perspective view of the first embodiment of the adjustable trial.

In this embodiment, upper platform 134 is located between adjustment platform 116 and upper support 138, as depicted in FIG. 5. Upper platform 134 has a projection 140 extending from lower surface 136. Projection 140 has an appropriate diameter to pass through central bore 124 of adjustment platform 116 into the non-threaded portion of bore 110 in lower platform 102. Projection 140 will have a notch 142 for engaging antirotation key 118 in bore 110 of the lower platform 102. The engagement of notch 142 with antirotation key 118 prevents the rotation of the upper platform 134 relative to the lower platform 102. Upper platform 134 can engage lower platform 102 in other ways to prevent their relative rotation. Therefore, adjustment platform 116 rotates relative to both the upper platform 134 and lower platform 102.

Figure 6:
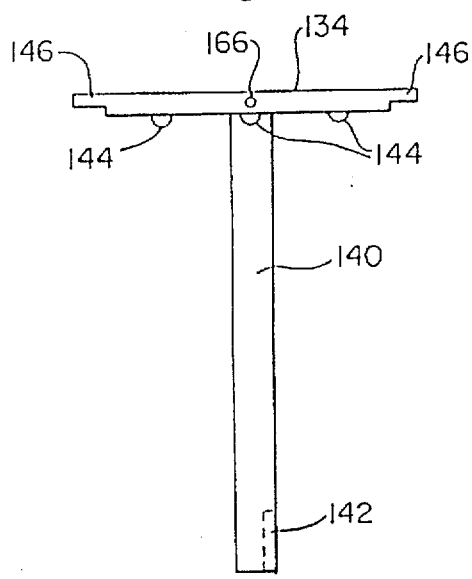
FIG. 6 is a front view of the upper platform of the first embodiment of the adjustable trial with the notch in the projection shown in phantom lines.
Figure 7:
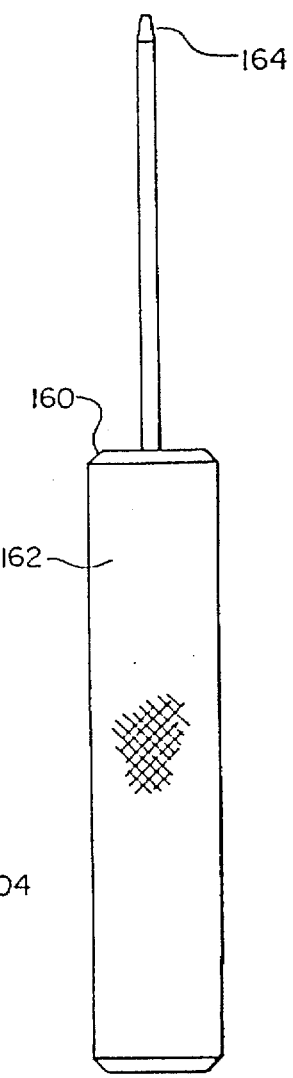
FIG. 7 is a side view of an advancing instrument.
Figure 9:
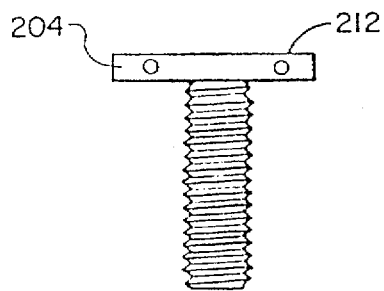
FIG. 9 is a front view of an adjustment platform of the second embodiment of the adjustable trial having a top with a flat surface.

As depicted in FIG. 2, upper platform 134 has four stop bosses 144 for engagement with stops 132 to resist rotation at one quarter turn increments. Stop bosses 144 are preferably semi-spherical protrusions from lower surface 136 of upper platform 134, as shown in FIG. 6. Upper platform 134 is preferably made from stainless steel or other suitable material.

Figure 3:
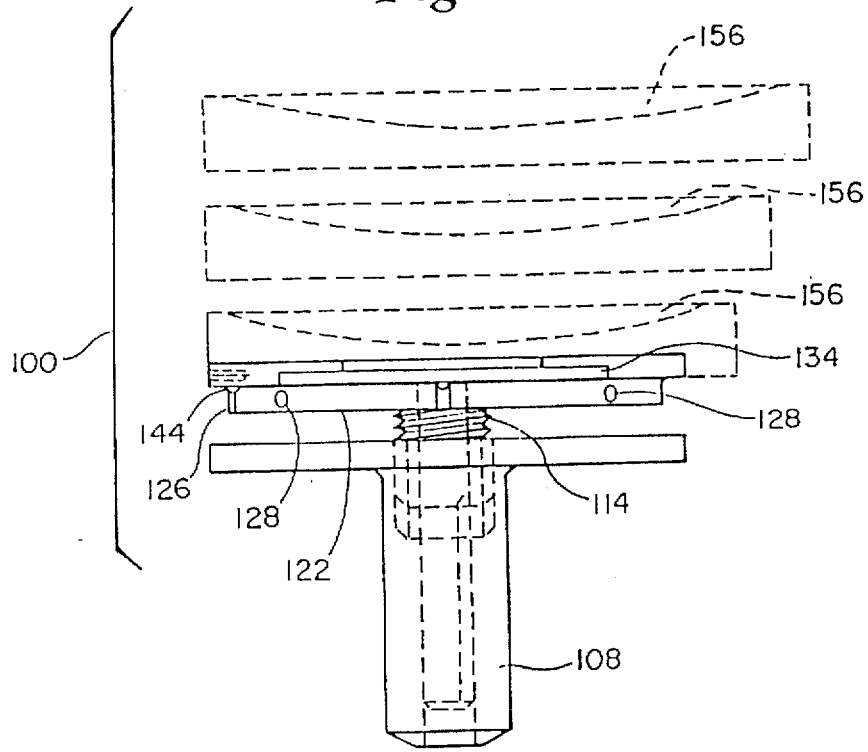
FIG. 3 is a side view of the first embodiment of the adjustable trial where some hidden features are shown in phantom lines and three different size upper supports are depicted with the two larger upper supports being displaced relative to their position on the adjustable supports.
Figure 4:
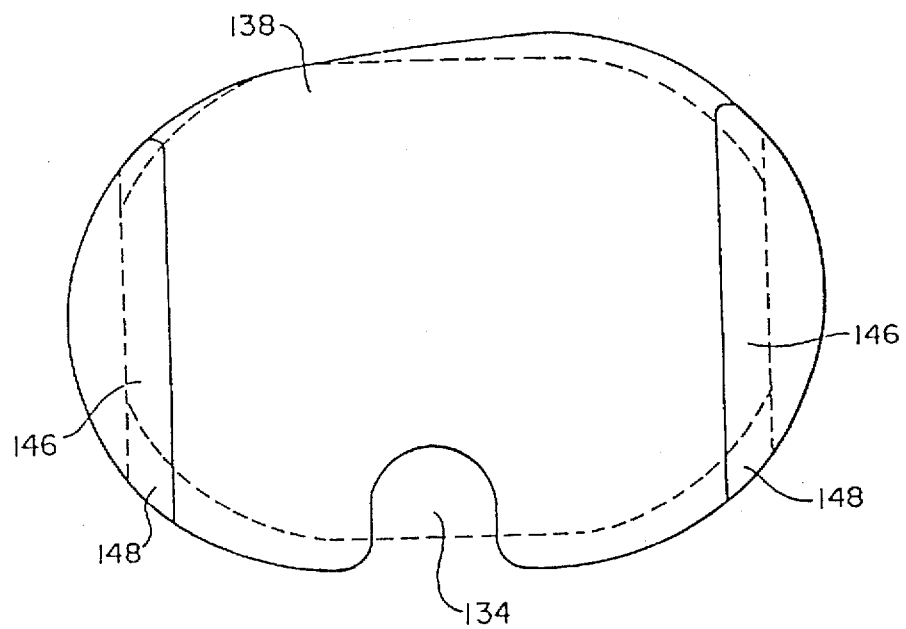
FIG. 4 is a bottom view of the upper support of the first embodiment of the adjustable trial with the outline of the upper platform shown in phantom.

Upper platform 134 has flanges 146 for slidable engagement with corresponding grooves 148 in upper support 138. The surgeon selects the proper size for the upper support 138 based on the size of the femoral component which is selected based on the sizes of the original tibia and femur. It is recognized that the upper support 138 can be removably attached to the upper platform 134 in a variety of alternative ways such as the engagement of various knobs (not shown) with slots (not shown) instead of using flanges 146 with grooves 148. The use of flanges 146 and grooves 148 is convenient because of the relative stability of the attachment while retaining the ease of replacement of the upper support 138 of the appropriate size. The phantom lines in FIGS. 1 and 3 give some indication of differences in sizes of the upper supports 138. Of course, in FIG. 1 the size of the upper support 138 would change on both sides roughly symmetrically.

The upper support 138 has a top surface 150 for engagement with the surface 152 of femoral component 154, as depicted in FIG. 27. The top surface 150 of upper support 138 has two depressions 156 that correspond with the artificial femoral condyles 158 of the femoral component 154. Upper support 138 preferably has a slight asymmetry of the two sides containing the two depressions 156 that depends on whether the component is designed for the left or right knee. Upper support 138 is preferably made from high density polyethylene such that there is relatively low friction engagement between the upper support 138 and femoral component 154, although other suitable materials can be used. The upper support 138 can be made from a hard polymer with photoelastic properties including lexan. When the upper support is constructed from a photoelastic material, visual inspection of the support can provide information on the force balance within the joint.

Advancing lever 130 can be replaced by a handled, advancing instrument 160 which has a handle 162 and a tip 164. The shape of the holes 128 are relatively unimportant as long as they allow engagement with advancing lever 130 or tip 164 of advancing instrument 160. Other advancing instruments may be used to rotate the adjustment platform, such as a ratchet mechanism or a lever with a contractable loop at one end similar to a device for removing an oil filter from car. The upper platform 134 has an attachment opening 166 for the attachment of an alignment bar (not shown). The alignment bar will have a projection to fit into attachment opening 166 and a long alignment portion that will be generally horizontal when the projection is fit into attachment opening 166. The alignment bar should be long enough to reach the ankle or hip of the patient depending on the orientation to be used for the alignment bar.

A second embodiment 200 of the adjustable trial is depicted in FIGS. 8–14. In this embodiment, lower platform 202 and adjustment platform 204 are similar to lower platform 102 and adjustment platform 116 of the first embodiment 100. The second embodiment 200 does not have the component corresponding to the upper platform 134 of the first embodiment 100. In the second embodiment 200, there is no need for adjustable platform 204 to have a central bore 140 as in adjustable platform 116 because there is no projection 140 to pass through the central bore 124. Also, adjustment platform 204 does not have stops 132, so there are no special orientations for rotating adjustment platform 204. Of course, the design can be modified to include the stops if desired. Similarly, there is no need for the unthreaded portion of bore 206 in lower platform 202.

In the second embodiment 200, upper support 208 replaces both the upper platform 134 and the upper support 138 of the first embodiment 100. The upper support 208 is selected to have the appropriate size for engaging the femoral component 154. Top surface 210 of upper support 208 is comparable to top surface 150 of the upper support 138 in the first embodiment.

Figure 10:
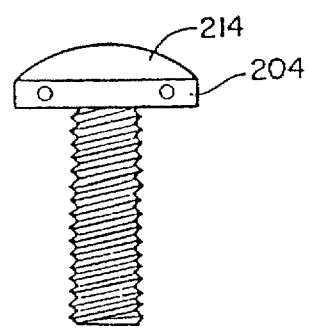
FIG. 10 is a front view of an adjustment platform of the second embodiment of the adjustable trial having a top with a domed surface.
Figure 8:
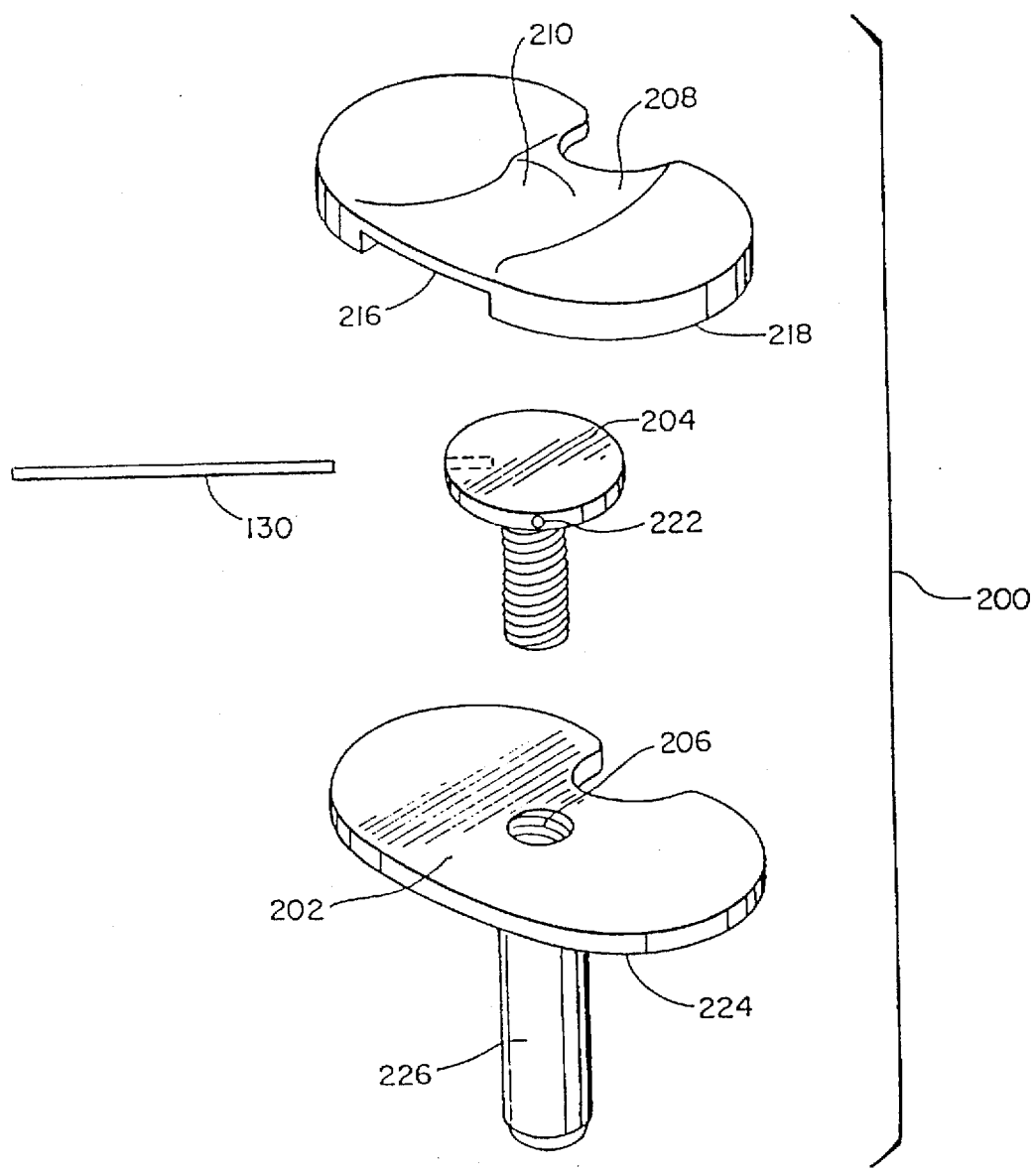
FIG. 8 is an exploded perspective view of a second embodiment of an adjustable trial.
Figure 11:
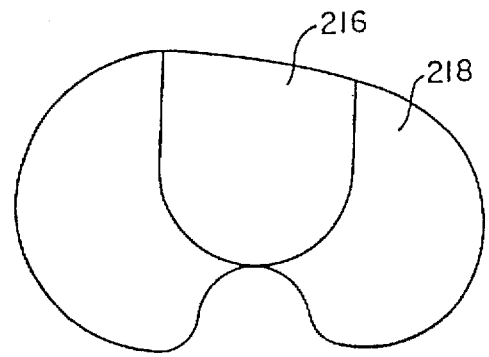
FIG. 11 is a bottom view of the upper support of the second embodiment of the adjustable trial adapted for a flat topped adjustment platform.
Figure 12:
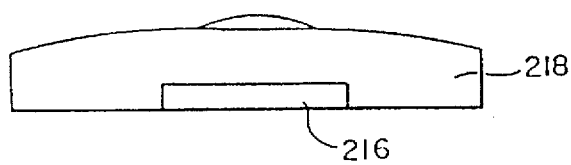
FIG. 12 is a front view of the upper support of the second embodiment of the adjustable trial adapted for a flat topped adjustment platform.
Figure 13:
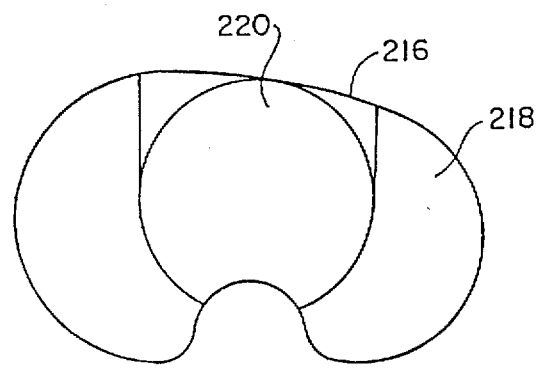
FIG. 13 is a bottom view of the upper support of the second embodiment of the adjustable trial adapted for a domed topped adjustment platform.
Figure 14:
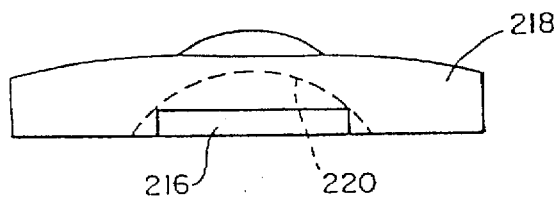
FIG. 14 is a front view of the upper support of the second embodiment of the adjustable trial adapted for a domed topped adjustment platform where the phantom lines indicate a sectional view at the maximum height of the cavity for fitting the domed adjustment platform.

Adjustment platform 204 may have various shaped tops, including a flat surface 212 (FIG. 9) or a domed surface 214 (FIG. 10). Upper support 208 has a slot 216 along the bottom surface 218, as shown in FIGS. 11 and 13. An adjustment platform 204 with a flat surface 212 fits into the slot 216 for engagement with the upper support 208. If appropriate, the bottom surface 218 of upper support 208 can have a domed indentation 220 to accept a domed surface 214 of adjustment platform 204, as shown in FIGS. 13 and 14. In either case, holes 222 for engaging advancing lever 130 or advancing instrument 160 are accessible through the opening of the slot 216. Upper support 208 does not have stop bosses. The adjustment platform 204 is preferably made from stainless steel, and the upper support 208 is preferably made from high density polyethylene, although other materials can be used.

The second embodiment 200 permits the relative rotation of the upper support 208 and the lower platform 202 along the screw axis since the adjustable trial 200 does not have the notch 142 and key 118 that prevented this rotation in the first embodiment 100. Furthermore, while the contact of the adjustment platform 204 having a flat surface 212 with the upper support 208 tends to hold the upper support 208 in the plane of the lower surface 224 of lower platform 202, this stability relative to tilting would be expected to be considerably less than the comparable stability in the first embodiment 100. When the adjustment platform 204 has a domed surface 214, the upper support is free to tilt relative to the lower platform 202.

The second embodiment 200 relies on the soft tissue surrounding the joint to hold the upper support 208 in the plane of the lower surface 224 of lower platform 202. The tilting of the upper support 208 relative to Me lower platform 202 reflects the balance or imbalance of Me soft tissues on either side of the joint. It is especially useful to use the domed surface 214 on adjustment platform 204. An absence of tilting reflects balanced soft tissues, while tilting indicates that Me tissues on one side are tighter Man on Me other side. The second embodiment 200 also has the advantage that a shorter post 226 can be used on the lower platform 202 relative to post 108, if desired, since the post 226 does not need to accommodate the projection 140 from the upper platform 134.

Figure 15:
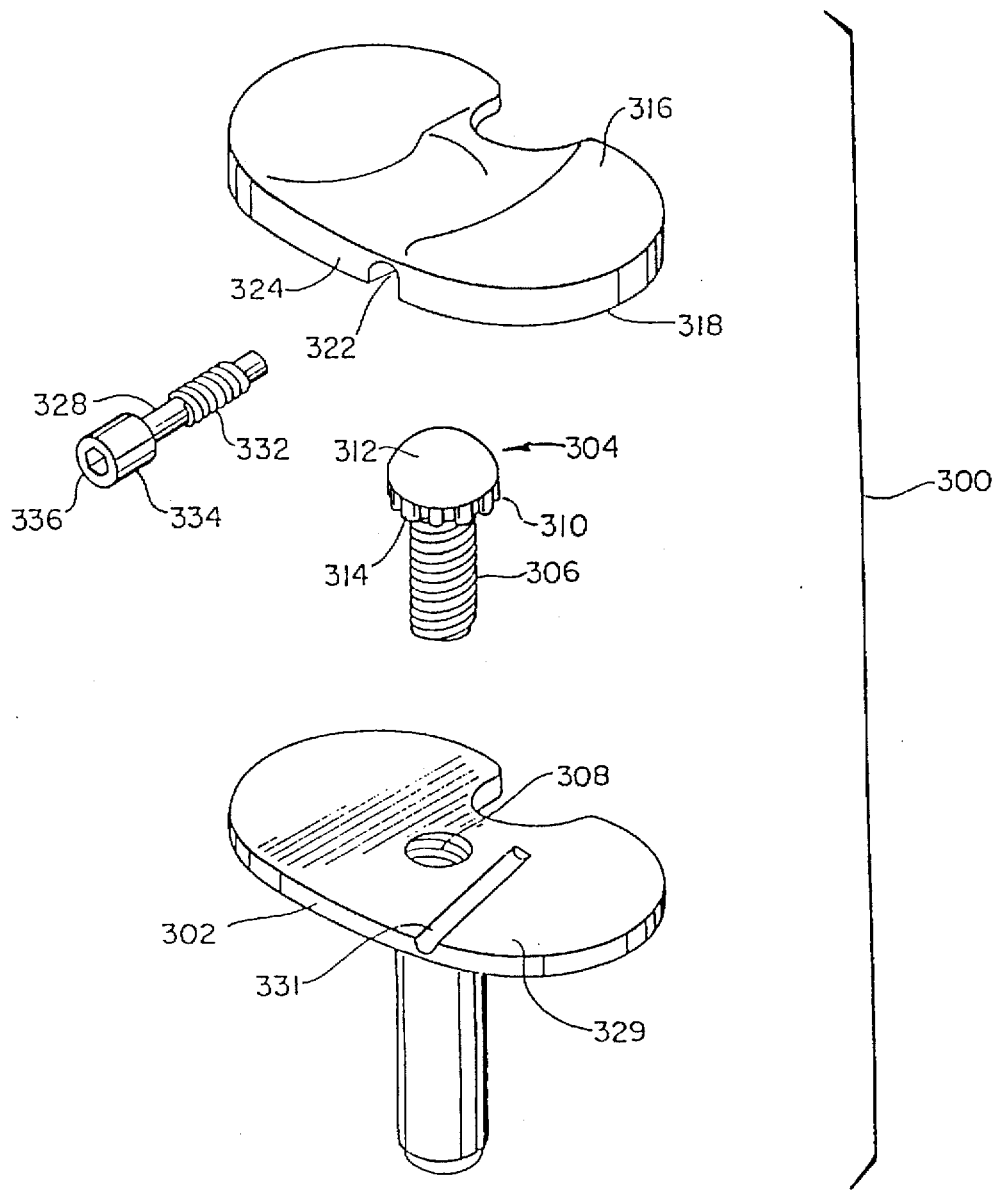
FIG. 15 is an exploded perspective view of a third embodiment of an adjustable trial using a worm gear to move the adjustment platform.
Figure 16:
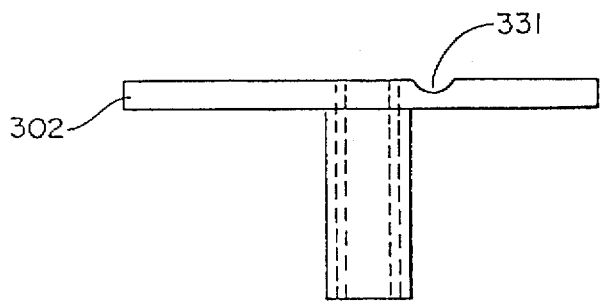
FIG. 16 is a front view of a lower platform of the third embodiment of the adjustable trial where phantom lines indicate a central bore.
Figure 17:
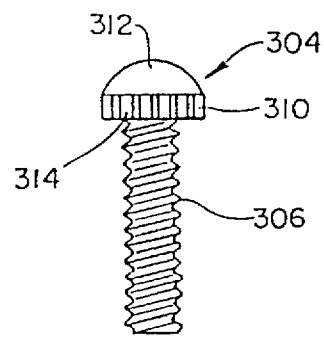
FIG. 17 is a side view of a threaded domed worm gear of the third embodiment of the adjustable trial.
Figure 18:
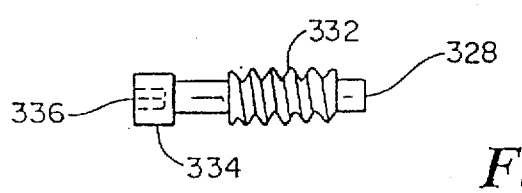
FIG. 18 is a side view of the worm of the embodiment of FIG. 15.

FIGS. 15–20 depict a third embodiment 300 of the adjustable tibial trial Embodiment 300 has a lower platform 302 with similar design considerations as the lower platform 202 from the second embodiment 200. The adjustable platform 204 is replaced with domed worm gear 304 with a threaded shaft 306, as shown in FIGS. 15 and 17. The threaded shaft 306 of worm gear 304 has threads to match the threads 308 of the lower platform 302. The top of the threaded domed worm gear 304 has a gear portion 310 and a dome 312. The dome can be replaced by other shaped tops such as a flat top comparable to the flat top 212 of the adjustment platform 204 in FIG. 9. The gear portion 310 has teeth 314. The worm gear 304 is preferably made from stainless steel, although other materials or combinations of materials can be used.

Figure 19:
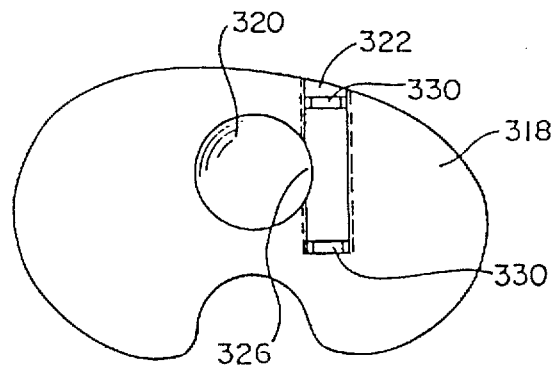
FIG. 19 is a bottom view of an upper platform of the third embodiment of the adjustable trial where the phantom lines indicate the larger extent of a partial cylindrical hole.
Figure 20:
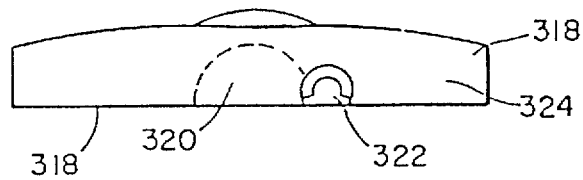
FIG. 20 is a front view of the upper platform of the third embodiment of the adjustable trial where the phantom lines indicate a sectional view at the maximal extent of the cavity for the domed top of the worm gear.

The upper support 316 is similar to the upper support 206 of the second embodiment 200. The bottom surface 318 of the upper structure 316 has a domed indentation 320, as shown in FIGS. 19 and 20. FIGS. 15, 19 and 20 depict a partial cylindrical hole 322 in the front 324 of upper support 316 which opens onto the bottom surface 318 along the length of the cylinder. The partial cylindrical hole 322 intersects with the domed indentation 320 at opening 326. The partial cylindrical hole 322 holds the worm 328 which is held in place by clips 330. The upper surface 329 of lower platform 302 also has a partial cylindrical hole 331 which fits a portion of the diameter of the worm 328 when the worm gear 304 is screwed far into lower platform 302.

Figure 21:
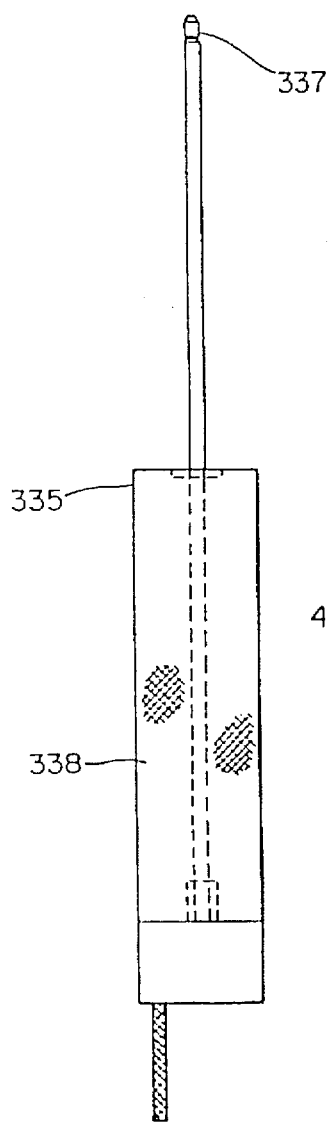
FIG. 21 is a side view of an hexagonal ball driver.

The worm 328 has a threaded region 332 and a head 334, as shown in FIG. 15. The head 334 of the worm 328 preferably has a hexagonal opening 336 for accepting an allen wrench (not shown) or a hexagonal ball driver 335 (FIG. 21) which has a hexagonal shaped tip 337 and a handle 338. The worm threads 332 and the teeth 314 of gear portion 310 meet at opening 326, shown in FIG. 19. The worm threads 332 and the teeth 314 are matched to rotate threaded portion 306 when the worm 328 is rotated. Therefore, the rotation of the worm 328 will alter the distance from the lower platform 302 to the upper support 316.

A reasonable selection for worm threads 332 provides quadruple threads yielding six teeth in 15 millimeters with a pitch diameter of 6.4 millimeters and a pitch of 2.5 millimeters. An appropriate worm gear 304 would have 18 teeth with a pitch diameter of 15 millimeters and pitch of 2.5 millimeters. The threaded stem of the worm gear would have an outer diameter of 9.5 millimeters, double threads and 11 threads per inch. One complete turn of the worm would lead to a one millimeter advancement of the threaded worm gear. Other combinations of design parameters could be used as well. The worm 328 is preferably made from stainless steel, although other materials are appropriate. Other types of gears, such as bevel gears or rack and pinion, could also be used.

As with the second embodiment 200, the upper support 316 can rotate relative to the lower platform 302. Also, the upper support 316 will be essentially free with respect to tilting from the plane defined by the lower platform 302. Any tilting of the upper support 316 will indicate that the forces on the two sides of the knee are not balanced.

Although not shown, a permanent tibial component may be selected according to the teachings of this invention. In the permanent tibial component, a tibial insert selected for the proper thickness and surface area may be rigidly attached to a permanent lower tibial platform. No relative rotation or tilting can occur between the permanent tibial insert and the lower tibial platform. In this sense, the first embodiment 100 of the adjustable trial most closely approximates the structure of the permanent tibial component. The second two embodiments provide more flexibility in assessing misalignment and force imbalance from the alignment of the trial itself. The second two embodiments can be most effectively used by surgeons who are able to take advantage of the instability of the trial to assist with aligning and balancing the forces of the knee.

Figure 22:
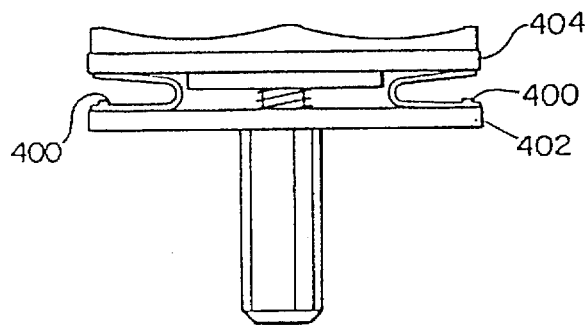
FIG. 22 is a front view of an adjustable trial tibial component with peripheral stabilizers with a relatively small distance between the lower platform and the upper support.
Figure 23:
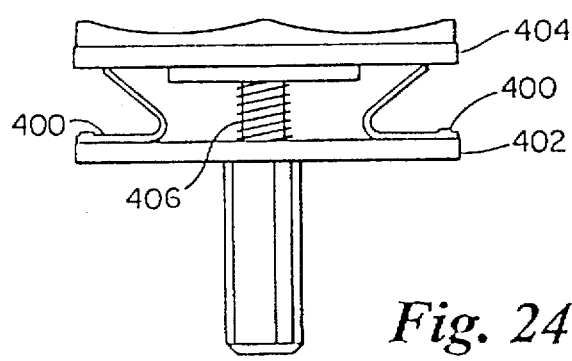
FIG. 23 is a front view of an adjustable trial tibial prosthesis with peripheral stabilizers with a relatively larger distance between the lower platform and the upper support.

If it is desirable to increase the stability of the second 200 and third 300 adjustable trials, springs 400 can be added to the peripheral edge between the lower platform 402 and the upper support 404, as shown in FIGS. 22 and 23. The springs 400 expand as the screw 406 is advanced to increase the width of the trial. Preferably four springs 400 would be used with one spring in the front, one in the back and one on each side, but other numbers of springs can be used. The springs 400 can also be used in the first embodiment 100 to compensate for any play in the connections that may allow some tilting of the upper support 138 relative to the lower platform 102. The surgeon will manually compress the springs 400 when placing the adjustable trial in place.

Figure 24:
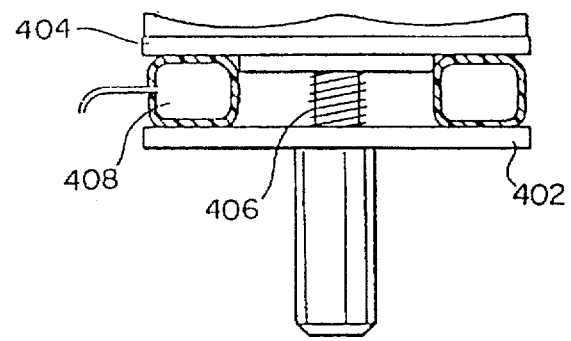
FIG. 24 is a front view of an adjustable trial with an inflatable bladder used as a peripheral stabilizer.

Similarly, an inflatable toroidal bladder 408 around the entire periphery of the upper support 404 can be used to provide the stability, as shown in FIG. 24. Air or another fluid is added or removed from the torotrial bladder 408 appropriately to have bladder 408 provide support between upper support 404 and lower platform 402. Other devices such as coil springs (not shown) can be used to provide peripheral stability. Moderation of the effects of soft tissue imbalance using a peripheral stabilizer may enhance the usefulness of the adjustable trial in balancing the soft tissue.

While the above three embodiments have a distance adjustment mechanism based on a screw to adjust the width of the trial, the screw can be replaced with other mechanisms. For example, the screw can be replaced with a ratchet mechanism similar to a car jack. The screw could be replaced by a rod with steps cut into it. The motion of a lever would advance the rod by one step at a time. A retractable flange would hold the rod in one position until advanced by the lever or until the flange is physically retracted to permit a decrease in the width of the trial. Such a ratchet mechanism would still require a post in the lower platform as a sleeve for the rod.

Figure 25:
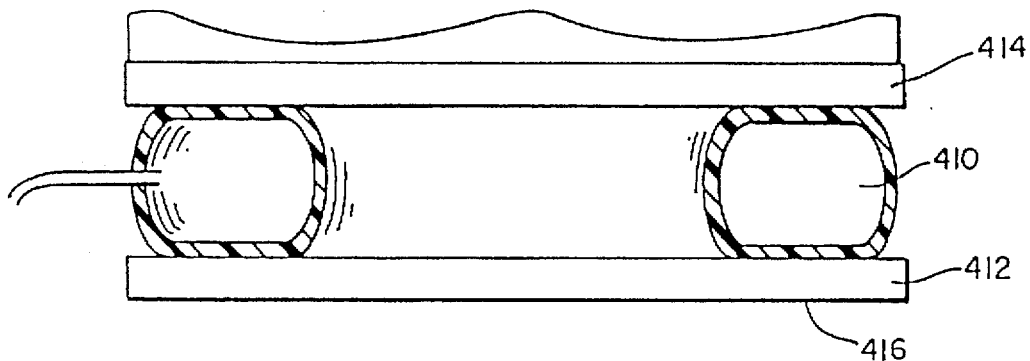
FIG. 25 is a front view of an adjustable trial without a lower post using an inflatable bladder for distance adjustment and peripheral stabilization.
Figure 26:
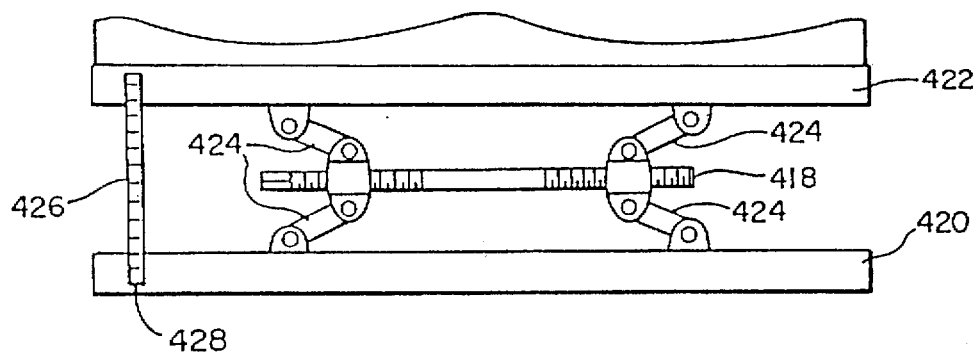
FIG. 26 is a front view of an adjustable trial without a lower post using a mechanical jack for a distance adjustment mechanism.

Other versions of the distance adjustment mechanism do not require the post, as shown in FIGS. 25 and 26. These versions of the adjustable trial would be most useful if the permanent tibial component does not have a corresponding post in the lower tray. For example, an inflatable toroidal bladder 410 can be used as a substitute for the screw in the advancing mechanism, as depicted in FIG. 25. In this embodiment, the adjustment platform is eliminated. The bladder 410 can be optionally glued or otherwise attached to either the lower platform 412 or the upper support 414 or both. Using the bladder 410 as the adjustment mechanism, various support structures can be placed on the bottom surface 416 of lower platform 412 to duplicate the support structures on the permanent tibial component. Similarly, a plurality of springs can substitute for the bladder 410.

Another example, shown in FIG. 26, would have a screw 418 oriented between the lower platform 420 and the upper structure 422. Rotation of the screw 418 would move levers 424 that would accordingly raise or lower the upper structure 422 relative to the lower platform 420. This example borrows from a different car jack design.

A surgeon using the adjustable trial component can determine the appropriate thickness for the permanent tibial insert while making accurate adjustments to the alignment of the knee and ligament tension. There are various ways of obtaining the tibial insert thickness. For the first embodiment 100 described above, the surgeon may count the number of quarter rotations between stops 132. Similarly, the second embodiment 200 and third embodiment 300 are designed to advance a known amount for a given rotation of the advancing mechanism. A correlation chart or a simple calculation can be used to obtain the tibial insert thickness from this number of rotations.

Alternatively, a ruler (not shown) can be used to make a measurement between marked points on the adjustable trial. This measurement can be used to obtain the tibial insert thickness. Another alternative would involve the removable attachment of a measuring device 426 (FIG. 26) at a slot 428 in the lower platform 420. The measuring device 426 can have markings to visually indicate the advancement of the upper support 422. The measuring device can be attached to the upper support 422 instead of the lower platform 420.

The use of the adjustable trial will depend on the exact design of the permanent prostheses and to some extent the choice of the surgeon. It is preferred that most if not all of the cutting of the bones takes place before the use of the adjustable trial. This usually involves cutting one or more flat surfaces on the end of each bone. Special cutters are typically used to ensure the cutting of a smooth, flat surface at the proper orientation. Necessary holes are also drilled. Sufficient cutting must be done to fit and stabilize the adjustable trial. The adjustable trial may require some cuts or holes that are not necessary for the permanent prosthesis. The design of the adjustable trial would preferably use many of the same surfaces and holes for its placement and stability as the permanent prosthesis. Any additional cutting or drilling that is needed for the placement of the permanent prosthesis but not the trial can be performed after the adjustments with the trial, but this additional cutting is preferably keep to a minimum.

Figure 29:
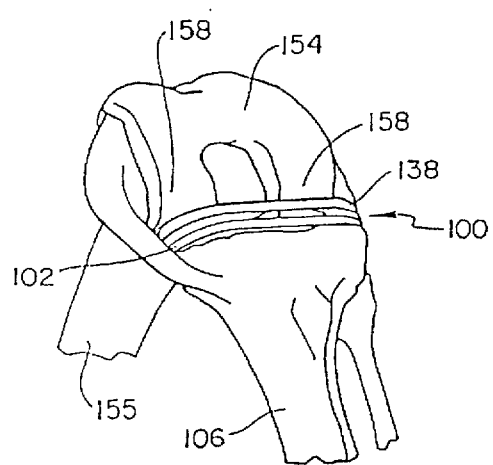
FIG. 29 is a perspective view of an adjustable trial in position in a knee with the leg in a flexed position.

Specifically, in the case of total knee arthroplasty, several cuts are usually performed on the femur since the femoral component 154 wraps around the end of the femur 155 to keep a portion of the component 154 in contact with the tibial component as the joint rotates. FIGS. 27 and 29 depict the different positions of the femoral component 154 relative to the adjustable trial 100 in the extended and flexed positions of the knee respectively. Several holes may be drilled to accommodate screws or pegs to secure the permanent prosthesis and/or to stabilize the cutting guide or trial.

The tibia is typically cut flat to accommodate its corresponding component. Again, several holes may be drilled to accommodate screws or pegs to secure the permanent component and/or to stabilize the cutting guide or trial. The permanent tibial component usually has a titanium or cobalt/chromium base that is attached to the tibia and polymer insert of variable width that is cemented or similarly attached to the base. The patella may also have a prosthesis on its inner surface.

The order of cutting the femur and tibia may depend on the particular prosthesis system used. The alignment and ligament balance may be checked prior to the placement of the adjustable trial in addition to being checked with the adjustable trial in place. Various possible apparatuses can be used to check the alignment and ligament balance including those described below.

Figure 28A:
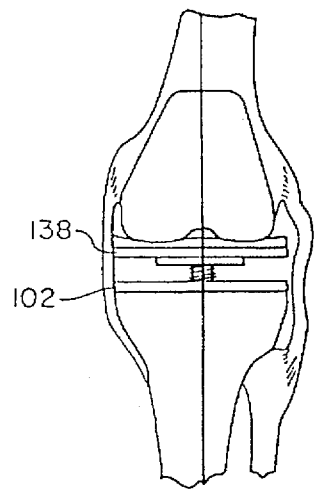
FIG. 28A is a front view of an adjustable trial in position in a knee.

Referring now to FIGS. 27 and 28A, after the necessary bone cutting is performed, the adjustable trial is put into place. When the joint is the knee, the patella must be moved out of the way while the trial is put in place, and comparable adjustments may be needed with other joints in order to put the trial prosthesis in place. The adjustable trial is put in place with the trial at its smallest thickness. With the joint in an extended position, the adjustable trial is expanded until some of the connective tissue is taught.

Figure 28B:
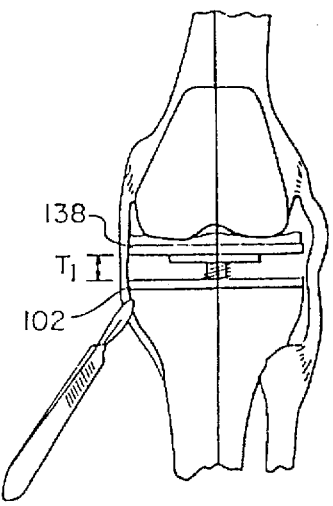
FIG. 28B is a front view schematically indicting a soft tissue release with an adjustable trial in place.
Figure 28C:
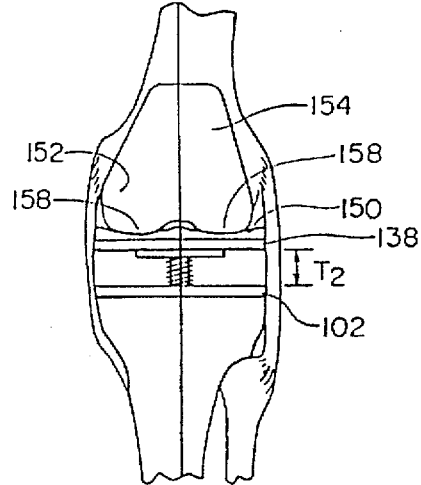
FIG. 28C is a front view depicting the adjustable trial in place in a knee with a somewhat larger distance between the tibial and the femoral components.

At this point, the balance of forces in the joint is checked. If the forces are not balanced, the connective tissue is adjusted accordingly through soft tissue releases, as represented in FIG. 28B. It may then be necessary to adjust the trial thickness after adjusting the connective tissue, from a first thickness $T_1$ shown in FIG. 28B, to a second thickness $T_2$ shown in FIG. 28C. If the trial thickness is changed, the balance of the connective tissue should be rechecked. The process is repeated until the trial thickness is adjusted appropriately at the same time that the forces are properly balanced.

The alignment of the joint is preferably checked frequently through the process and must be correct at the end of the adjustment process. The alignment is preferably also checked in the flexed position shown in FIG. 29. The joint should smoothly flex with the adjustable trial in place. Embodiments 2 and 3 with tiltable components, or an instrumented trial component with force transducers would allow tissue balance and alignment to be continuously monitored over the range of flexion and extension.

Figure 30:
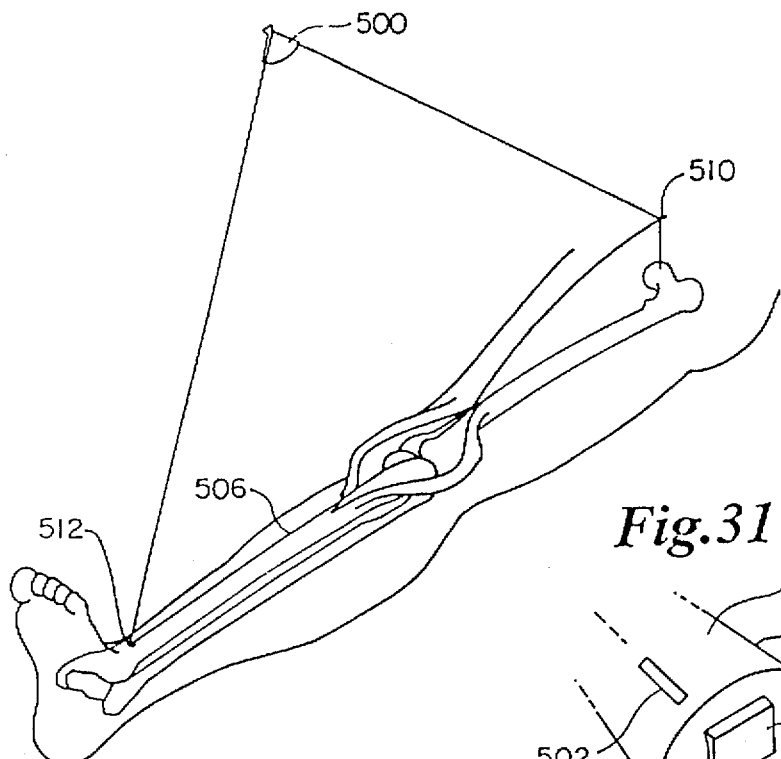
FIG. 30 is a perspective, schematic view of a leg during knee surgery where a line of light is available for aligning the leg.
Figure 31:
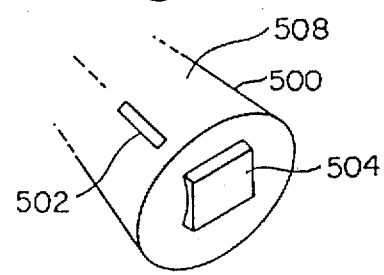
FIG. 31 is a partial cut away perspective view of a light strip alignment device.

Standard ways of aligning the knee use various forms of metal rods, which are awkward and inefficient. This awkwardness results in a surgeon often relying on visual evaluation of alignment without using the metal rod for many of their preliminary alignment determinations. FIGS. 30 and 31 show a light strip alignment device 500 of the present invention which has none of the awkwardness of the metal rod. While the light strip alignment device 500 is out of the way of the surgeon performing the complicated manipulations to the joint, it is immediately available to check alignment when needed.

Light strip alignment device 500 has a strong light source 502. A laser is particularly convenient to use for the light source 502 because the laser beam is well collimated. Incandescent bulbs or other similar light sources can be used for the light source 502 if appropriate optics are used to collimate the light. With a laser for the light source 502, a cylindrical lens 504 can be used to spread the beam in one direction while keeping the beam well collimated in a perpendicular direction. Other optics can be used with the laser light source if needed. In this way, a line of light 506 is produced that is long in one direction and very thin in the other direction. Light source 502 and cylindrical lens 504 can be conveniently placed in a housing 508.

Light strip alignment device 500 is preferably placed on the ceiling or wall of the procedure room. The alignment device 500 is out of the way of the surgeon when mounted on the ceiling. The alignment device 500 can be optionally placed on a stand if preferred to make it easier to position the alignment device. It is preferred that the light shine down vertically so that the line of light will look straight on the curved surface of the leg when looking directly down at the leg.

The line of light 506 is positioned similarly to the metal rod. When aligning a knee joint, a point of the line of light is positioned to strike the point 510 on the upper leg above the center of the femoral head, and another point of the line of light is positioned to strike the center of the ankle 512. Then, the line of light 506 should pass through the center of the knee when the knee is properly aligned. Any other portion of the musculo-skeletal system can be comparably aligned.

The operating room can be arranged for the alignment of the line of light 506 in a variety of ways. The alignment device 500 can be mounted in the ceiling in a fixed orientation. The operating table can then be positioned to place the limb in roughly the correct alignment. The surgeon would then place the limb in the correct position when ready to measure alignment. Alternatively, the alignment device 500 can be mounted so that it can be rotated to change the orientation of the line of light 506 or even shiftable to center the alignment device 500 over the correct portion of the patient. The alignment device 500 can be positioned manually using a handle (not shown) or mechanically using a motor drive (not shown) with a control means operated by the surgeon or an assistant.

Alignment device 500 can be used effectively for many types of arthroplasty on many different joints. The alignment is preferably checked frequently during the surgery. The alignment is preferably checked, at least, every time the forces within the joint are balanced. With frequent checking of the alignment, it may be convenient to leave the alignment device 500 on during the whole surgery. Alternatively, the alignment device can be turned on and off at appropriate points in the surgery to conserve energy and to avoid distraction by the light when it is not needed.

Figure 32:
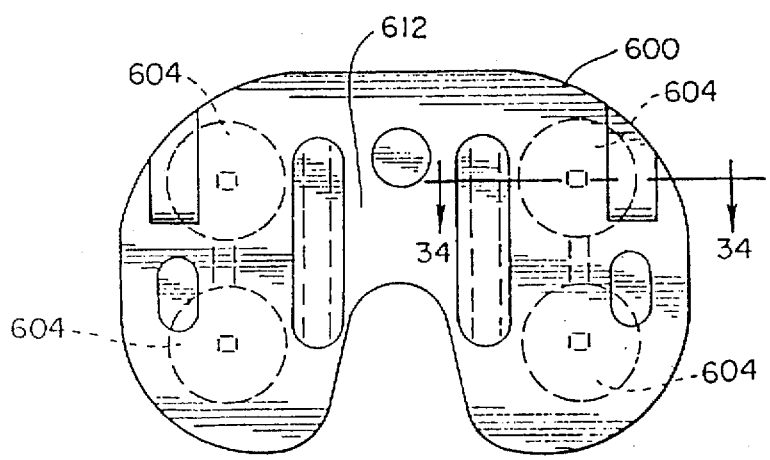
FIG. 32 is a top view of a transducer unit that is applied to the bottom of an upper support of an adjustable trial with phantom lines indicating internal structures for force transducers and associated wiring.
Figure 33:
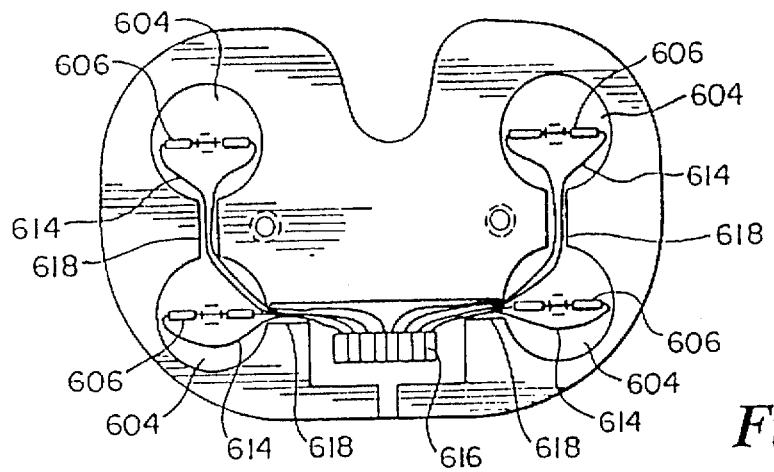
FIG. 33 is a bottom view of the transducer unit.
Figure 34:
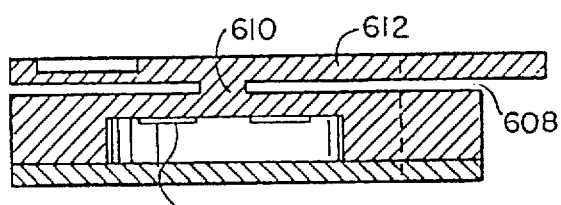
FIG. 34 a sectional view of the transducer unit taken along line 34 of FIG. 32.

Except for the visual guidance provided by the tiltable adjustable trials 200 and 300 and the information provided from the alignment bar, if used, the instruments of the invention described above do not provide the surgeon with assistance in balancing ligament forces. However, there are instruments within the invention to meet this need. First, the force transducers of U.S. Patent 5,197,488 can be adapted for use in an adjustable trial. In the adaptation involving the first embodiment 100 of the adjustable trial, a transducer unit 600 is included with the upper platform 134, as shown in FIG. 32. Forces within the knee are transmitted from the upper support 138 to the transducer unit 600. Transducer unit 600 contains force transducers to provide measurements of the forces within the knee prostheses. FIGS. 32-34 focus on structures suitable for using strain gauges 606 as the force transducers. Other arrangements are possible using different designs of transducers.

Transducer unit 600 contains a plurality of cavities 604. Four cavities 604 can be conveniently used to distinguish relative anterior and posterior forces and left and right forces with a possible arrangement shown in FIG. 32. Strain gauges 606 are placed at the top of each cavity 604. Resistive or piezo-electric strain gauges 606 can be used. Transducer unit 600 is machined to produce a spacing layer 608 which is open except at specific posts 610, shown in FIG. 34.

Posts 610 will be positioned directly above the center of strain gauges 606 to direct the forces to the strain gauges 606. Posts 610 will connect with flexing cover 612 above the cavities 604 to provide additional support. Additional posts 610 can be located away from cavities 604. The size of the posts 610 should be adjusted to yield the appropriate magnitude of forces at the strain gauges 606. Transducer unit 600 is preferably constructed from a combination of stainless steel for rigid support, especially in the vicinity of projection 612, and an elastic material, such as high density polyethylene, especially for regions conducting force to the strain gauges 606 including flexing covers 612.

Electrical wires 614 connect strain gauges 606 to connector 616. Channels 618 provide room for the wires to reach connector 616. Connector 616 should be connected to a resistance meter (not shown) in the case of a resistance strain gauge to separately measure the output of each strain gauge. Connector 616 could also be connected to a brige circuit and amplifier (not shown) to measure the output of the strain gauges on a transducer as a group.

The output of the resistance meters or bridge circuits and amplifiers can be output directly to a display or sent to an analog-to-digital converter (not shown) for input into a computer (not shown). A radio transmitter (not shown) can be placed at various points in the system to replace some of the wire connections. Other types of force transducers can easily be interfaced appropriately. The force transducer can comprise essentially the entire upper support when the upper support is made from a photelastic material such as lexan. Visual inspection of the photoelastic material could provide immediate information on the force imbalances within the joint.

Figure 35:
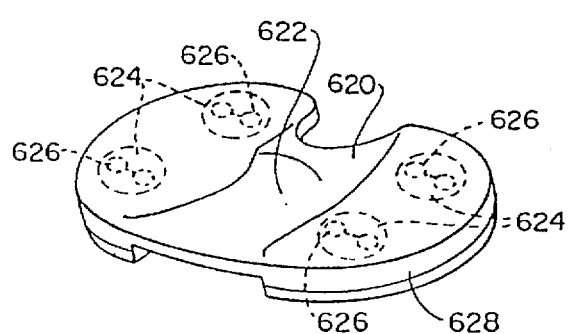
FIG. 35 is top perspective view of a transducer support unit with phantom lines depicting cavities containing strain sensors.

Similarly, the upper supports of any of the other embodiments are suitable for adapting with force transducers. In these cases depicted in FIG. 35, the upper supports are replaced with transducer support units 620. The top surface 622 the transducer support unit 620 is designed for contact with a femoral component. Transducer support unit 620 is also fitted with appropriate structures to interact with the particular adjustment mechanism. Transducer support units 620 will have cavities 624 with strain gauges 626 at the top of the cavities 624. The transducer support units 620 will be produced with spacing layers 628 which are empty except for posts (not shown) similar to the construction of the spacing layer 608 in transducer unit 600. Transducer support unit 620 can be produced from high density polyethylene or some other comparable material with some elasticity. Different numbers of strain gauges can be used. One large transducer with at least two strain gauges can be used where the transducer is symmetrically disposed within the transducer support unit.

Figure 36:
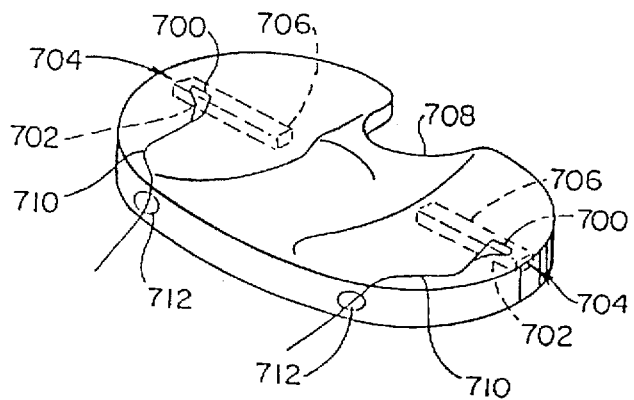
FIG. 36 is a perspective view of an alternative embodiment of an upper platform adapted with force sensors, with the force transducers shown in phantom lines.

Another configuration of force transducers is shown in FIG. 36. This configuration eliminates the need for large cavities 624 and a spacing layer 628. To measure the difference between the medial and lateral contact forces, a strain gauge 700 is mounted on either the upper or lower surface at the end of two rectangular pieces of metal 702 forming two transducers 704. These transducers 704 are placed in grooves 706 machined into the underside of the upper platform 708 in a medial-lateral direction, such that the strain gauges are located at a roughly equal distance from the center of the upper platform 708. The transducer 704 can be fixed in place within the grooves 706 with glue or epoxy to ensure continuity between the polyethylene of the upper platform 708 and the transducer 704.

The lead wires 710 from strain gauges 700 are passed from the upper platform 708 through channels 712. The wires 710 from the two sides of upper platform 708 are connected to the adjacent arms of a Wheatstone bridge circuit (not shown) to yield differences between the measured strains. If the soft tissues on the sides of the knee are balanced, the contact forces in the upper platform will be roughly equal, and the strains will be correspondingly roughly equal causing a cancellation in the bridge circuit. If the soft tissues are not balanced, the contact forces will not be equal, and the contact forces on the tight side will be larger than the contact forces on the loose side. This inequality in contact forces results in an imbalance in the strains with greater strain on the tight side and an output from the bridge circuit that increases with the strain.

Figure 37A:
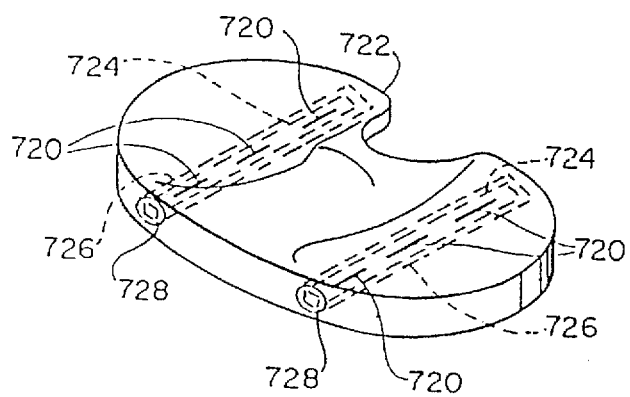
FIG. 37A is perspective view of a second alternative embodiment of an upper platform adapted with force sensors, with the force transducers depicted with phantom lines.
Figure 37B:
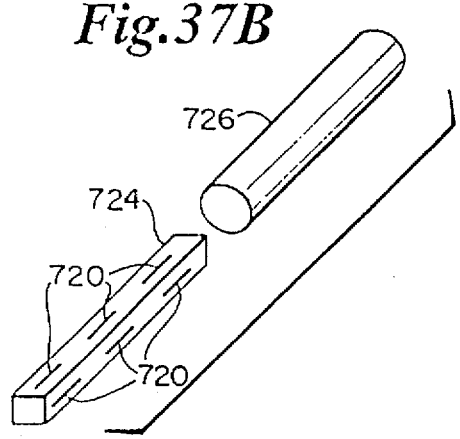
FIG. 37B is a perspective view of depicting the force transducers and a cylindrical tube into which they are placed.

Multiple pairs of strain gauges 720 can be used, and the transducer can be made in other geometries and from other materials. FIG. 37 displays an embodiment with multiple pairs of strain gauges 720. The use of multiple pairs of strain gauges 720 permits the measurement of the magnitude and location of the contact forces on the medial and lateral sides of the upper platform 722. In the embodiment of FIG. 37, three pairs of strain gauges 720 are mounted diametrically opposite on the top and bottom surfaces of a rectangular metal tube 724. Each top and bottom strain gauge pair 720 are connected to adjacent arms of a Wheatstone bridge such that their output is additive. The instrumented rectangular tube 724 is placed within a cylindrical tube 726 with the strain gauges in the gap between the rectangular 724 and cylindrical tubes 726 for protection. The gap is filled with epoxy or other filler to ensure continuity between the strain gauges 720 and the upper platform 722.

Two cylindrical tubes 726 are placed in tunnels 728 within the upper platform 722. The tunnels 728 are oriented in the transverse plane for sensing the location of the contact forces in both the medial-lateral and anterior-posterior directions on the articular upper surface of the upper platform 722. The number of pairs of strain gauges 720 can be varied within the constraint of the size. The strains in the transducer gauges 720 can be calibrated to obtain the related contact forces. More pairs of strain gauges 720 increase the resolution of the measured contact forces. Other strain sensing elements such as piezoelectric transducers can be used. One force transducer with several strain gauges could be used extending across the upper platform 722 in a medial-lateral orientation.

One significant advantage of using transducers in the trial is that the forces can be continuously monitored in a variety of orientations of the joint including both flexed and extended positions and positions in between. The surgeon has flexibility to decide how many force readings to take. The measurements can be performed quickly. Furthermore, the forces within the joint directly provide the information needed by the surgeon to properly balance the soft tissues surrounding the joint.

Figure 38:
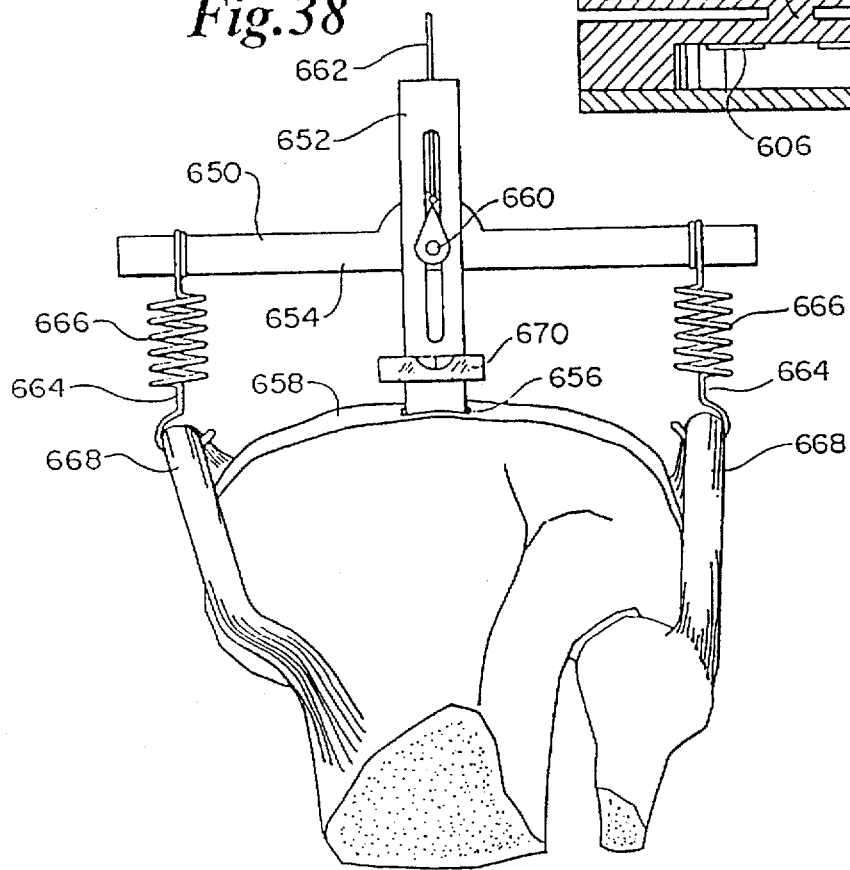
FIG. 38 is a front perspective view a soft tissue balance being used to balance the ligaments of a knee.

Another instrument within the invention for balancing forces near a joint is a peri-articular soft tissue balance 650. FIG. 38 displays such a balance being used with collateral knee ligaments and/or other associated soft tissue. The balance 650 has an upright support 652 and a pivot arm 654. Preferably, the end of the upright support 652 inserts into a slot 656 in the lower platform 658 of any embodiment of an adjustable trial or standard trial prosthesis. Attaching the upright support 652 to the lower platform 658 provides support for the balance and provides a point of reference even if the knee is tilted. The pivot arm 654 is attached to the upright support 652 at hinge 660. Hinge 660 should have low friction. The pivot arm 654 has a pointer 662 attached perpendicular to a line running along the length of the pivot arm 654 where the pointer is oriented along a line going through hinge 660.

The pivot arm 654 is balanced such that it will naturally hang in a horizontal orientation. Two fasteners 664 are positioned on pivot arm 654 on opposite sides of the arms symmetric relative to the hinge 660. Fasteners 664 preferably have springs 666 to provide flexibility for attaching fasteners 664 to ligaments 668. The springs 666 should be matched so that measured imbalances should be due to imbalances in ligament tension rather than imbalances in spring constants. The patella must be moved to the side in the extended position to provide the space needed to insert upright support 652 into slot 656.

When tensions are equal, pointer 662 (or other suitably engineered indicia) will point along upright support 652. If ligament tensions are not equal, the surgeon performs a soft tissue release of the tighter ligament to bring its tension in conformity with the other ligament. Small errors will result if the knee is tilted slightly such that the upright support 652 is not vertically oriented. These errors should be small because the force from the ligament tension should be much greater than the forces due to the imbalance in the weight for the pivot arm 654. Optionally, a level 670 can be placed on the upright support 652 providing the surgeon with a way to level the knee prior to balancing the ligament tensions.

Instead of attaching the upright support 652 to the lower platform 658, the upright support can be suspended just above the patient from above. The difficulty with this arrangement is that there is no check on the orientation of the knee to ensure that a measured imbalance is due to rotation of the knee rather than an imbalance in ligament tension. One possible way of dealing with this difficulty is to use slot 656 or some other suitable structure for the placement of a small level (not shown) on lower platform 658. It may be possible to have the patella in place even with the small level attached to the lower platform 658, although it may be difficult to read the small level with the patella in place. Alternatively, surgeons can level the knee relying on their own observations.

While the soft tissue balance 650 would not be expected to be as accurate as the force transducer 600, the ligament balance is particularly simple and inexpensive while still providing valuable feedback. Furthermore, the ligament balance has the advantage over sensors in a trial prosthesis because it can be used in situations where the joint is not being replaced. But, the force transducer 600 measures the magnitude of the contact force, while the soft tissue balance 650 indicates only the balance or imbalance of the tissues, not the magnitude. Soft tissue balance 650 only provides information on the balance of the two ligaments and does not provide information on the absolute value of the tension in the ligaments. Also, the force transducer reflects the imbalance of all of the tissue surrounding the joint not just a portion such as the ligaments that can be easily attached.

Various modifications and alterations of this invention will become apparent to those skilled in the art without departing from the scope and spirit of this invention.

We claim:

1. An adjustable tibial trial prosthesis for use in accurately sizing and positioning a permanent prosthesis during surgery on a human knee joint comprising:

(a) a first surface comprising an upper platform for operative engagement with a distance adjustment mechanism and a slidable upper support, said slidable upper support designed for movable engagement with an artificial surface consisting of a femoral component at the distal end of a femur such that the joint can flex, said slidable upper support having a size based on the size of the human femur in the joint for which it is designed;

(b) a second surface for engaging the end of the tibia, where the ends of the femur and tibia meet at the joint; and (c) a reversible distance adjustment mechanism to vary the distance between the first surface and the second surface while the tibial trial prosthesis is in the joint during surgery, said adjustment mechanism comprising means operable in a first direction to lengthen the distance between the first and the second surface and operable in a second direction to shorten the distance between the first and second surface while maintaining said first surface in a fixed rotational orientation relative to the joint, and where the first surface, the second surface, and a length of the distance adjustment mechanism between said first and second surface facilitate the, accurate sizing and positioning of surfaces on a permanent prosthesis to be selected and attached at the end of the tibia.

2. The adjustable trial prosthesis of claim 1 wherein the first surface can tilt relative to the second surface in response to unbalanced forces on the first surface.

3. The adjustable trial prosthesis of claim 2 further comprising a peripheral stabilizer to supply force tending to maintain the relative orientation of the first surface and the second surface.

4. The adjustable trial prosthesis of claim 1 wherein said second surface includes at least one post for insertion into at least one hole in the tibia.

5. The adjustable trial prosthesis of claim 1 wherein the distance adjustment mechanism comprises a screw engaged with and rotationally uncoupled from one of the surfaces and threads mated with the screw operably attached to the other surface such that rotation of the screw relative to the threads changes the distance between the first and second surfaces.

6. The adjustable trial prosthesis of claim 5 further comprising stops which provide increased resistance to rotation at selected angular orientations of the screw.

7. The adjustable trial prosthesis of claim 1 where the first surface is operably coupled to a notch and the second surface is operably coupled to a key and where the engagement of the key with the notch resists the relative rotations of the first and second surfaces.

8. The adjustable trial prosthesis of claim 1 wherein the distance adjustment mechanism comprises an expandable fluid filled bladder.

9. The adjustable trial prosthesis of claim 1 further comprising at least one force transducer whereby forces within the joint are measured.

10. The adjustable trial prosthesis of claim 9 wherein the at least one force transducer is comprised of at least one strain sensor located to measure strain at representative locations across the adjustable trial.

11. A method of using an adjustable tibial trial prosthesis for selecting the size of a knee joint permanent prosthesis comprising the steps (a) placing an adjustable tibial trial prosthesis within the knee joint where the adjustable tibial trial prosthesis has:

a first surface comprising an upper platform for operative engagement with a distance adjustment mechanism and an upper support, said upper support designed for movable engagement with an artificial surface consisting of a femoral component at the distal end of a femur such that the joint can flex, said upper support having a size based on the size of the human femur in the joint for which it is designed;

a second surface for engaging the end of the tibia, where the ends of the femur and tibia meet at the joint; and a reversible distance adjustment mechanism to vary the distance between the first surface and the second surface while the tibial trial prosthesis is in the joint during surgery;

(b) adjusting the distance adjustment mechanism to obtain appropriate tensions within and around the joint by operation of adjustment means operable in a first direction to lengthen the distance between the first and the second surface and operable in a second direction to shorten the distance between the first and second surface while maintaining said first surface in a fixed rotational orientation relative to the joint; and (c) determining from fie the first surface, the second surface, and a length of the distance adjustment mechanism between said first and second surface, after adjustment of the tibial trial prosthesis, the appropriate size of permanent prosthesis to be selected and attached at the end of the tibia.

\* \* \* \* \*

UNITED STATES PATENT AND TRADEMARK OFFICE
CERTIFICATE OF CORRECTION

PATENT NO. : 5,733,292
DATED : March 31, 1998
INVENTOR(S) : Ramon B. Gustilo, Joan Bechtold, Richard S. Hammett, William D. Lew It is certified that error appears in the above-identified patent and that said Letters Patent is hereby corrected as shown below:

Column 5, line 26, delete "from" and insert --front--.
Column 11, line 2, delete "Me" and insert --the--.
Column 11, line 3, delete "Me" and insert --the--.
Column 11, line 7, delete "Me" and insert --the--
(2 occurrences).
Column 11, line 7, delete "Man" and insert --than--.
Column 11, line 14, insert "." between "trial" and "Embodiment".
Column 12, line 37, delete "torotrial" and insert --toroidal--.
Column 15, line 45, unbold "5,197,488".
Column 20, line 10, insert "of:" after "steps".
Column 20, line 37, delete "fie" between "from" and "the".

Signed and Sealed this

Fifteenth Day of May, 2001

Attest:

NICHOLAS P. GODICI

Attesting Officer    Acting Director of the United States Patent and Trademark Office